(12) United States Patent
Kato

(10) Patent No.: US 8,067,666 B2
(45) Date of Patent: Nov. 29, 2011

(54) MODEL ANIMAL CAUSING THE WHITE HAIR DEVELOPMENT AND METHODS RELATING THERETO

(75) Inventor: Masashi Kato, Kasugai (JP)

(73) Assignee: Chubu University Educational Foundation, Kasugai-Shi (JP)

( * ) Notice: Subject to any disclaimer, the term of this patent is extended or adjusted under 35 U.S.C. 154(b) by 485 days.

(21) Appl. No.: 11/988,203

(22) PCT Filed: Feb. 10, 2006

(86) PCT No.: PCT/JP2006/302783
§ 371 (c)(1),
(2), (4) Date: Jan. 30, 2008

(87) PCT Pub. No.: WO2007/004337
PCT Pub. Date: Jan. 11, 2007

(65) Prior Publication Data
US 2009/0083864 A1    Mar. 26, 2009

(30) Foreign Application Priority Data
Jul. 1, 2005   (JP) ................. 2005-193425

(51) Int. Cl.
*A01K 67/00* (2006.01)
*A01K 67/027* (2006.01)
*C12P 21/06* (2006.01)
*C12N 5/00* (2006.01)
*C12N 15/00* (2006.01)

(52) U.S. Cl. ......... 800/18; 800/4; 800/8; 800/9; 800/14; 800/21; 435/69.1; 435/320.1; 435/325; 435/455

(58) Field of Classification Search ................. 800/4, 18
See application file for complete search history.

(56) References Cited

U.S. PATENT DOCUMENTS
7,105,717 B1   9/2006 Shirai et al.

FOREIGN PATENT DOCUMENTS
JP   9-131146       5/1997
JP   2001-231402    8/2001

OTHER PUBLICATIONS

Matsushima et al. Mammalian Genome 13:30-35; 2002.*
Kato et al. Oncogene 17: 1885-1888; 1998.*
Kumasaka et al. Cancer Res. 70:24-29; 2010.*
Slominski et al Journal of Investigative Dermatology 124:13-21, 2005.*

* cited by examiner

*Primary Examiner* — Sumesh Kaushal
(74) *Attorney, Agent, or Firm* — Jordan and Hamburg LLP

(57) ABSTRACT

A model rodent animal with a phenotype in which hair growing after birth is black, with the animal spontaneously developing white hair after aging. By way of example, the model rodent animal may have a genotype in which an activated RET gene is genetically inserted in a heterozygous form and the endothelin receptor B gene is deficient in a heterozygous form.

3 Claims, 2 Drawing Sheets

(1)  (2)  (3)  (4)

A1  A2  A3  A4  B  C

SEQUENCE LISTING

```
<160> NUMBER OF SEQ ID NOS: 2

<210> SEQ ID NO 1
<211> LENGTH: 1542
<212> TYPE: DNA
<213> ORGANISM: Homo sapiens

<400> SEQUENCE: 1
atggcctccg ggagtgtggc cgagtgcctg cagcaggaga ccacctgccc cgtgtgcctg      60
```

```
cagtacttcg cagagcccat gatgctcgac tgcggccata acatctgttg cgcgtgcctc      120
gcccgctgct ggggcacggc agagactaac gtgtcgtgcc cgcagtgccg ggagaccttc      180
ccgcagaggc acatgcggcc caaccggcac ctggccaacg tgacccaact ggtaaagcag      240
ctgcgcaccg agcggccgtc ggggcccggc ggcgagatgg cgtgtgcga gaagcaccgc       300 gagcccctga agctgtactg cgaggaggac cagatgccca tctgcgtggt gtgcgaccgc      360
tcccgcgagc accgcggcca cagcgtgctg ccgctcgagg aggcggtgga gggcttcaag      420
gagcaaatcc agaaccagct cgaccattta aaaagagtga agatttaaa gaagagacgt       480 cgggcccagg ggaacaggc acgagctgaa ctcttgagcc taacccagat ggagagggag       540
aagattgttt gggagtttga gcagctgtat cactccttaa aggagcatga gtatcgcctc      600
ctggcccgcc ttgaggagct agacttggcc atctacaata gcatcaatgg tgccatcacc      660
cagttctctt gcaacatctc ccacctcagc agcctgatcg ctcagctaga agagaagcag      720
cagcagccca ccagggagct cctgcaggac attggggaca cattgagcag ggctgaaaga      780
atcaggattc ctgaaccttg gatcacacct ccagatttgc aagagaaaat ccacattttt      840
gcccaaaaat gtctattctt gacggagagt ctaaagcagt tcacagaaaa aatgcagtca      900
gatatggaga aaatccaaga attaagagag gctcagttat actcagtgga cgtgactctg      960
gacccagaca cggcctaccc cagcctgatc ctctctgata atctgcggca agtgcggtac     1020
agttacctcc aacaggacct gcctgacaac cccgagaggt tcaatctgtt tccctgtgtc     1080
ttgggctctc catgcttcat cgccgggaga cattattggg aggtagaggt gggagataaa     1140
gccaagtgga ccataggtgt ctgtgaagac tcagtgtgca gaaaaggtgg agtaacctca     1200
gcccccagag atggattctg ggcagtgtct ttgtggtatg ggaaagaata ttgggctctt     1260
acctccccaa tgactgccct accctgcgg accccgctcc agcgggtggg gattttcttg     1320
gactatgatg ctggtgaggt ctccttctac aacgtgacag agaggtgtca caccttcact     1380
ttctctcatg ctacctttg tgggcctgtc cggccctact tcagtctgag ttactcggga     1440
gggaaaagtg cagctcctct gatcatctgc cccatgagtg ggatagatgg gttttctggc     1500
catgttggga atcatggtca ttccatggag acctcccctt ga                       1542

<210> SEQ ID NO 2
<211> LENGTH: 1329
<212> TYPE: DNA
<213> ORGANISM: Mus musculus

<400> SEQUENCE: 2
atgcaatcgc ccgcaagccg gtgcggacgc gccttggtgg cgctgctgct ggcctgtggc       60 ttcttgggg tatggggaga gaaaagagga ttcccacctg cccaagccac gctgtcactt      120
ctcgggacta agaggtaat gacgccaccc actaagacct cctggaccag aggttccaac       180
tccagtctga tgcgttcctc cgcacctgcg gaggtgacca aggagggag gggggctgga      240 gtcccgccaa gatccttccc tcctccgtgc caacgaaata ttgagatcag caagactttt      300
aaatacatca cacgattgt gtcgtgcctc tgttcgtgc taggcatcat cgggaactcc       360
acgctgctaa gaatcatcta caagaacaag tgcatgcgca atggtcccaa tatcttgatc      420
gccagtctgg ctctgggaga cctactgcac atcatcatag acatacccat taacacctac      480
aagttgctcg cagaggactg gccatttgga gctgagatgt gtaagctggt gcccttcata      540
cagaaggctt ctgtgggaat cacagtgctg agtctttgtg ctctaagtat tgacagatat      600
cgagctgttg cttcttggag tcgaattaaa ggaattgggg ttccaaaatg gacagcagta      660
```

```
gaaattgttt taatttgggt ggtctctgtg gttctggctg tccccgaagc cataggtttt    720
gatatgatta cgtcggacta caaaggaaag cccctaaggg tctgcatgct taatcccttt    780
cagaaaacag ccttcatgca gttttacaag acagccaaag attggtggct gttcagtttc    840
tacttctgct tgccgctagc catcactgca gtcttttata ccctgatgac ctgcgaaatg    900
ctcaggaaga agagcggtat gcagattgct ttgaatgatc acttaaagca gagacgagaa    960
gtggccaaga cagtcttctg cctggtcctc gtgtttgctc tctgttggct tccccttcac   1020
ctcagccgga tcctgaagct caccctgtat gaccagagca atccacacag gtgtgagctt   1080
ctgagctttt tgttggtttt ggactacatt ggtatcaaca tggcttcttt gaactcctgc   1140
atcaatccaa tcgctctgta tttggtgagc aaaagattca aaaactgctt taagtcatgt   1200
ttgtgctgct ggtgccaaac gtttgaggaa aagcagtcct tggaggagaa gcagtcctgc   1260
ctgaagttca aagccaacga tcacggatat gacaacttcc ggtccagcaa taaatacagc   1320
tcgtcttga                                                           1329
```

MODEL ANIMAL CAUSING THE WHITE HAIR DEVELOPMENT AND METHODS RELATING THERETO

BACKGROUND OF THE INVENTION

1. Field of the Invention

The present invention relates to a model animal causing the white hair development, a method for establishing a model animal causing the white hair development, a method for successively growing a model animal causing the white hair development, a method for making research works about the white hair development, a screening method of means for controlling the white hair development, and a composition for controlling the white hair development.

More specifically, the invention relates to those described below:

(a) a model animal with a phenotype such that the color of the hair first growing after birth is black or almost black but the model animal causes the spontaneous onset of white hair development following aging;

(b) a method for establishing the model animal by a combination of a specific genetic manipulation procedure and a mating;

(c) a method for successively growing the model animal by mating together the resulting model animal to obtain a progeny of the model animal, which progeny has the same phenotype as that of the model animal;

(d) a method for making research works about the white hair development by utilizing such model animal;

(e) a method for screening for means for controlling the onset of white hair development (means for preventing/suppressing or promoting the white hair development), where the screening procedure is carried out as a part of such research works; and (f) a composition for controlling the onset of white hair development, which composition contains a substance preventing/suppressing or promoting the white hair development as the component for controlling the white hair development, where the substance preventing/suppressing or promoting the white hair development is obtained by the screening.

2. Description of the Related Arts

In recent years, progresses have been made in the technique for preparing transgenic animals with extraneous functional genes introduced therein and in the genetic targeting technique utilizing homologous recombination of genes in ES cells and the like. Owing to these techniques, then, various model animals have been proposed, by which various human diseases and the like can be simulated for experiments and research works.

Generally, model animals for such purposes are preferably mammalian animals biologically close to humans. In particular, small mammalian animals typically including rodents such as mouse and rat are relatively readily available and usable, so these small mammalian animals are the most suitable in view of their rapid growth and their rapid alterations of generations.

[Literature 1] Official Gazette of JP-A-9-131146
[Literature 2] Official Gazette of JP-A-2001-231402

The Literature 1 and the Literature 2 disclose examples of such animals. Specifically, the Literature 1 discloses a transgenic rat with the impairment of sperm generation because of the introduction of the c-myc gene therein under the control of the metallothionein IIA promoter. The Literature 2 discloses a model rat causing the onset of prostate cancer, where a transgene prepared by conjugating the gene of the SV40 large T antigen to the downstream of the rat probacin gene promoter was introduced. As described above, the model animals proposed in the related art are overwhelmingly animals in relation with serious human diseases such as cancer and diabetes mellitus.

Alternatively, a field exists for aesthetic problems or problems about outward appearances in no relation with human health or death, but the fundamental causes or countermeasures of the problems have not yet been elucidated. Nonetheless, a large market of related products so as to overcome or avoid those problems is generated. A typical example thereof is the problem of white hair development following aging of humans with dark-colored hairs such as black hair and brown hair.

Specifically, a great number of people are bothered with the white hair development following aging in view of aesthetics and appearance. Therefore, hair dyes are now making a large market. However, hair dying is only a simple appearance modification so dying should be repeated when hair grows only at a low level. Because dying requires laborious works every time of hair growing, hair dying does not sufficiently satisfy users.

For example, pharmaceutical products expressing an effect of preventing white hair development or food products commonly considered effective for preventing white hair development are found in general. Since the mechanism of the white hair development has not yet been elucidated, however, the effects of these pharmaceutical products or food products lack scientific grounds. Furthermore, persons continuously incorporating these pharmaceutical products and food products have diverse genetic dispositions and have very diverse dietary life styles in so diverse environments. Thus, it is hard to observe any statistic or empirical reliability in the effects of these pharmaceutical products and food products.

An effective experimental means for making research works about the mechanism of the white hair development in humans when provided will make a dramatic progress in the research works and development of the white hair development and means for controlling the white hair development (means for preventing/suppressing or promoting the white hair development). Any model animal preferable from the standpoint of the white hair development following aging, of which the color of the hair first growing after birth is black or almost black, would potentially be the effective experimental means. However, such model animal has not yet been provided or proposed actually.

SUMMARY OF THE INVENTION

It is an object of the invention to provide a model animal preferable in view of the white hair development (a model animal as a small mammalian animal). It is an additional object of the invention to promote the research works about the white hair development and the development of means for controlling the onset thereof, using the model animal preferable in view of the white hair development.

A first aspect of the invention is a model animal causing the white hair development, which is a non-human mammalian animal with a phenotype such that the color of the hair first growing after birth is black or almost black but the model animal causes the spontaneous white hair development following aging.

In case of mouse, for example, hair first grows almost one week after birth.

The model animal causing the white hair development in the first aspect has a characteristic phenotype such that the color of the hair first growing after birth is black or almost black but spontaneously causes increasing white hair development following aging. The characteristic feature is the same as the human white hair development, where humans with dark hairs such as black, dark brown or flaxen hairs have spontaneously causes increasing white hair development following aging. Furthermore, it is suggested that the mechanism of the white hair development in humans would essentially be the same as the mechanism thereof in the model animal, since humans and the model animal are both mammalian animals.

It is almost surely suggested that a finding about means for controlling the white hair development in humans and at least a potent reference finding thereabout will be obtained from the research works about the mechanism of the white hair development, using the model animal causing the white hair development. The means for controlling the white hair development includes means for preventing the white hair development, means for suppressing the onset thereof or means for promoting the onset thereof.

In case that the various findings described above are obtained, various compositions for controlling white hair development may be developed with scientific grounds and reliability based on experiments. Such compositions for controlling white hair development may contain as the active components, a substance for preventing the white hair development, a substance for suppressing the white hair development, a substance for promoting the white hair development or a substance antagonistic against the substance for promoting the white hair development. Furthermore, a treatment effective for controlling the white hair development or environmental conditions therefor may expectantly be found. Accordingly, the model animal in view of the white hair development in accordance with the first aspect is potentially an attractive research tool for pharmaceutical companies, cosmetic manufacturers, food product manufacturers, medical device manufacturers, and various service companies for health and aesthetics.

In a second aspect of the invention, the model animal in view of the white hair development in accordance with the first aspect has a gene type, where (1) the activated RET gene is genetically inserted in a hetero form and (2) the endothelin receptor B (Ednrb) gene is deficient in a hetero form, or the Ednrb gene is deficient in the homo form or in a hetero form and the Ednrb gene is genetically inserted in the homo form or in a hetero form under the dopamine beta-hydroxylase (DbH) promoter.

More preferably, the model animal causing the white hair development has a gene type, where (1) the activated RET gene is genetically inserted in a hetero form and (2) the Ednrb gene is deficient in a hetero form, or the Ednrb gene is deficient in the homo form or in a hetero form and the Ednrb gene is genetically inserted in the homo form or in a hetero form under the DbH promoter.

In Literature 3 described below, model mice with the activated RET gene genetically inserted therein including mice with the RET gene genetically inserted therein in hetero forms are known. Those model mice include transgenic mouse lines established as the line 304, the line 192 or the line 242. However, the color of the hair in any of those transgenic mice never changes throughout their lives, although some have a phenotype of black colored skin over the whole body in the time of birth.

[Literature 3] Takashi Iwamoto, Masahide Takahashi, Masafumi Ito, Kiyohiro Hamatani, Masaharu Ohbayashi, Worawidth Wajjwalku, Ken-ichi Isobe, Izumi Nakashima, "Aberrant melanogenesis and melanocytic tumor development in transgenic mice that carry a metallothionein/ret fusion gene", The EMBO Journal vol. 10, no. 11, pp. 3167-3176 (1991).

In Literature 4 and the like described below, gene targeting mice with deficiency in the Ednrb gene in a hetero form or the homo form are known. However, the color of the hair in any of those gene targeting mice never changes throughout their lives.

[Literature 4] Kiminori Hosoda, Robert E. Hammer, James a. Richardson, Amy Greenstein Baynash, Jason C. Cheung, Adel Giaid, Masashi Yanagisawa, "Targeted and Natural (Piebald-Lethal) Mutations of Endothelin-B Receptor Gene Produce Megacolon Associated with Spotted Coat Color in Mice", Cell Vol. 79, 1267-1276, Dec. 30 (1994)

Therefore, it is absolutely never anticipated from the transgenic mouse with the activated RET gene genetically inserted therein or from the gene targeting mouse with deficiency in the Ednrb gene that the model animal (for example, model mouse) with the gene type in the second aspect has a phenotype such that the color of the hair first growing after birth is black or almost black but the model animal causes the white hair development following aging. It is totally never anticipated from a conceptual combination of the transgenic mouse and the gene targeting mouse.

In a third aspect of the invention, the activated RET gene in the second aspect is the hybrid gene between the RET finger protein (RFP) gene and the activated RET gene, namely RFP-RET.

The RFP gene is known. Any type of the activated RET gene may be satisfactory with no specific limitation, which is for example RFP-RET in the third aspect.

In the fourth aspect of the invention, the activated RET gene in the second aspect or in the third aspect is conjugated with the metallothionein I(MT) gene as the promoter.

In the model animal causing the white hair development in the second aspect or in the third aspect, the activated RET gene is conjugated with a promoter appropriately selected in terms of the animal species of the model animal and the like, for insertion into the gene. According to experiments made by the present inventor, preferably, the RET gene is conjugated with the promoter region of the metallothionein I gene for genetic insertion, in case that the model animal is for example a rodent animal such as mouse and rat.

In a fifth aspect of the invention, the non-human mammalian animal in any of the first through fourth aspects of the invention is a rodent animal.

The species of the non-human mammalian animal as the model animal causing the white hair development is not specifically limited but a rodent animal is particularly preferably. Rodent animals are small mammalian animals and relatively readily available and usable, with a rapid growth and a rapid alteration of generations.

In a sixth aspect of the invention, the rodent animal in the fifth aspect of the invention is mouse or rat.

The species of the rodent animal in the fifth aspect of the invention is not specifically limited. Mouse or rat with accumulated handling knowledge as the model animal species is particularly preferable.

A seventh aspect of the invention is a method for establishing a model animal causing the white hair development in any of the first through sixth aspects of the invention by mating the RET-transgenic animal with the activated RET gene inserted genetically in a hetero form therein as a non-human mammalian animal with an Ednrb gene-modified animal as the same species of the non-human mammalian animal, where the Ednrb gene is deficient in a hetero form, or the Ednrb gene is deficient in the homo form or in a hetero form and the Ednrb gene is genetically inserted in the homo form or in a hetero form under the DbH promoter, to obtain the model animal causing the white hair development.

The inventor found that by mating the RET-transgenic animal with the activated RET gene inserted genetically in a hetero form therein as a non-human mammalian animal with an Ednrb gene-modified animal as the same species of the non-human mammalian animal, where the Ednrb gene is deficient in a hetero form, or the Ednrb gene is deficient in the homo form or in a hetero form and the Ednrb gene is genetically inserted in the homo form or in a hetero form under the DbH promoter, the model animal causing the white hair development in the progeny (F1) generation could be obtained.

As the results of the analysis of the gene type, the inventor found that the model animal causing the white hair development had a gene type, where (1) the activated RET gene was genetically inserted in a hetero form and (2) the Ednrb gene was deficient in a hetero form, or the Ednrb gene was deficient in the homo form or in a hetero form and the Ednrb gene was genetically inserted in the homo form or in a hetero form under the DbH promoter.

Not any non-human mammalian animal with such phenotype has been known in the related art. Therefore, it is suggested that the phenotype is defined by the gene type, where (1) the activated RET gene is genetically inserted in a hetero form and (2) the Ednrb gene is deficient in a hetero form, or the Ednrb gene is deficient in the homo form or in a hetero form and the Ednrb gene is genetically inserted in the homo form or in a hetero form under the DbH promoter.

It can be said alternatively that a model animal with such gene type even when the model animal is generated by means except the parent mating described above can have the phenotype as the model animal causing the white hair development. Thus, a method for establishing a model animal causing the white hair development in the twelfth or thirteenth aspect of the invention is also established.

According to the Mendel's genetic rule, herein, mating of the RET-transgenic animal with the activated RET gene inserted genetically in a hetero form therein with the Ednrb gene-targeting animal with the Ednrb gene deficiency in a hetero form generates F1 generations with the following four gene types (1) through (4), individually at a ¼ probability.
(1) RET/+·Ednrb (+/−): the gene type where the activated RET gene is inserted genetically in a hetero form while the Ednrb gene is deficient in a hetero form.
(2) RET/+·Ednrb (+/+): the gene type where the activated RET gene is inserted genetically in a hetero form while the Ednrb gene is not deficient.
(3) +/+·Ednrb (+/−): the gene type where the activated RET gene is never inserted while the Ednrb gene is deficient in a hetero form.
(4) +/+·Ednrb (+/+): the gene type where the activated RET gene is never inserted while the Ednrb gene is never deficient.

The F1 generation where the activated RET gene is genetically inserted in the homo form never reaches delivery, because of disorders in the development. Additionally, the F1 generation with the gene type described above in (4) is a wild-type mouse with not any gene modification.

The F1 generations with the gene types described in (2), (3) and (4) cannot be used as the model animal causing the white hair development, because the black hair first growing after birth in the generations scarcely changes.

In preparing an animal with a modification in the Ednrb gene, animals with deficiency in the Ednrb gene in the homo form die due to megacolon within several months after birth.

Megacolon can be prevented in the animals with deficiency in the Ednrb gene in the homo form, by genetically inserting the Ednrb gene in the homo form or in a hetero form under the known DbH (dopamine beta-hydroxylase) promoter to be expressed in a manner specific to the tissue of intestinal ganglion. Additionally, megacolon never emerges in the animals deficient in the Ednrb gene in a hetero form, when genetic insertion of the Ednrb gene in the homo form or in a hetero form under the DbH promoter is done therein. These animals with the Ednrb gene genetically inserted therein in the homo form or in a hetero form under the DbH promoter can be prepared by genetically inserting DNA conjugated with the Ednrb gene under the DbH promoter into a fertilized animal egg.

Such mouse can be utilized as an animal with a modification in the Ednrb gene as a mating parent. A method for preventing megacolon in an animal with a knock-out animal of the Ednrb gene in the homo form has already been known in the Literature 5 below, where examples using rats are described.
[Literature 5] Gariepy C E, Ohuchi T. Williams S C, Richardson J A, Yanagisawa M.,
"Salt-sensitive hypertension in endothelin-B receptor-deficient rats", J. Clin. Invest. 2000 April; 105(7):925-33.

In an eighth aspect of the invention, the RET-transgenic animal in the seventh aspect is an MT/RET-transgenic animal where the activated RET gene conjugated with the metallothionein I(MT) gene as the promoter is inserted genetically in a hetero form.

As the RET-transgenic animal for use as one parent in the seventh aspect, the MT/RET-transgenic animal with the activated RET gene conjugated with the metallothionein I gene as the promoter, as inserted genetically therein in a hetero form, can be used.

In a ninth aspect of the invention, the non-human mammalian animal in the seventh aspect or in the eighth aspect is a rodent animal.

The species of the non-human mammalian animal as the model animal causing the white hair development is not specifically limited but particularly preferably, the non-human mammalian animal is a rodent animal as a small mammalian animal with a rapid growth and a rapid alteration of generations, which is readily available and usable.

In a tenth aspect of the invention, the rodent animal in the ninth aspect is mouse or rat.

The species of the rodent animal in the ninth aspect is not specifically limited. Particularly preferably, the rodent animal is mouse or rat with accumulated handling knowledge as such type of model animals.

In an eleventh aspect of the invention, the RET-transgenic animal or the MT/RET-transgenic animal in any of the seventh aspect through the tenth aspect is an RET-transgenic mouse or an MT/RET-transgenic mouse established as the line 304, the line 304/B6, the line 192 or the line 242.

The species or line of the RET-transgenic animal or the MT/RET-transgenic animal in the seventh aspect through the tenth aspect is not specifically limited. As described in the following Examples, however, an RET-transgenic mouse or an MT/RET-transgenic mouse established as the line 304, the line 304/B6, the line 192 or the line 242 can preferably be used.

In a twelfth aspect of the invention, a method for establishing a model animal causing the white hair development so as to obtain the model animal causing the white hair development in any of the first aspect through the sixth aspect is provided, the method including a genetic targeting manipulation procedure by allowing the Ednrb gene of the RET-transgenic animal or the MT/RET-transgenic animal defined in any of the seventh aspect through the eleventh aspect to be deficient in a hetero form or a gene modification procedure by allowing the Ednrb gene of the RET-transgenic animal or the MT/RET-transgenic animal defined in any of the seventh aspect through the eleventh aspect to be deficient in the homo form or in a hetero form and then genetically inserting the Ednrb gene in the homo form or in a hetero form under the DbH promoter.

The characteristic phenotype of the model animal causing the white hair development is defined by the gene type "where (1) the activated RET gene is genetically inserted in a hetero form and (2) the Ednrb gene is deficient in a hetero form, or the Ednrb gene is deficient in the homo form or in a hetero form and the Ednrb gene is genetically inserted in the homo form or in a hetero form under the DbH promoter". Such gene type can be realized by means other than the mating between the RET/transgenic animal as defined in the seventh aspect and the defined Ednrb gene-modified animal. As described in the twelfth aspect, for example, a model animal causing the white hair development and having such gene type can be established by a gene targeting manipulation procedure comprising allowing the Ednrb gene of the RET-transgenic animal or the MT/RET-transgenic animal to be deficient in a hetero form or by a gene modification procedure comprising allowing the Ednrb gene of the RET-transgenic animal or the MT/RET-transgenic animal to be deficient in the homo form or in a hetero form and then genetically inserting the Ednrb gene in the homo form or in a hetero form under the DbH promoter.

In a thirteenth aspect of the invention, a method for establishing a model animal causing the white hair development is provided, the method comprising a gene insertion manipulation procedure by genetically inserting the activated RET gene in an Ednrb gene-modified animal defined in any of the seventh aspect through the eleventh aspect in a hetero form, to obtain the model animal causing the white hair development in any of the first invention through the sixth invention. The Ednrb gene-modified animal is a gene-modified animal where the Ednrb gene is deficient in a hetero form, or the Ednrb gene is deficient in the homo form or in a hetero form and the Ednrb gene is genetically inserted in the homo form or in a hetero form under the DbH promoter.

Due to the same reason as in the twelfth aspect, a model animal causing the white hair development with the gene type, "where (1) the activated RET gene is genetically inserted in a hetero form and (2) the Ednrb gene is deficient in a hetero form, or the Ednrb gene is deficient in the homo form or in a hetero form and the Ednrb gene is genetically inserted in the homo form or in a hetero form under the DbH promoter", can be established by a gene insertion manipulation procedure for genetically inserting the activated RET gene in the Ednrb gene-modified animal in a hetero form.

In a fourteenth aspect of the invention, the activated RET gene conjugated with the metallothionein I gene as the promoter is used in the gene insertion manipulation procedure of the activated RET gene in the thirteenth aspect.

In the gene insertion manipulation procedure of the activated RET gene in the thirteenth aspect, the metallothionein I gene is conjugated as the promoter to prepare the MT/RET-transgene, which is particularly preferably inserted genetically.

A fifteenth aspect of the invention is a method for successively growing a model animal causing the white hair development comprising mating the model animal causing the white hair development in any of the first aspect through the sixth aspect for stably growing the model animal causing the white hair development in any of the first aspect through the sixth aspect.

The model animal causing the white hair development in the first aspect through the sixth aspect can be established by various methods in the seventh aspect through the fourteenth aspect. By mating these model animals together, the model animal causing the white hair development can be grown and maintained in a stable manner.

According to the Mendel's rule, it can be said that by mating together the model animal causing the white hair development, the probability of obtaining the model animal causing the white hair development with the gene type "where (1) the activated RET gene is genetically inserted in a hetero form and (2) the Ednrb gene is deficient in a hetero form, or the Ednrb gene is deficient in the homo form or in a hetero form and the Ednrb gene is genetically inserted in the homo form or in a hetero form under the DbH promoter" is substantially ⅓, from the standpoint that the insertion of the activated RET gene in the homo form causes lethal death.

In a sixteenth aspect of the invention, a method for making research works about the white hair development is provided, the method comprising making research works about the mechanism of the white hair development using the model animal causing the white hair development in any of the first aspect through the sixth aspect or making research works about the influence on the white hair development by administering a given substance or a given treatment to the model animal causing the white hair development.

As described in the sixteenth aspect, research works about the mechanism of the white hair development or research works about a factor controlling the white hair development can be done, using the model animal causing the white hair development. By the term "factor controlling the white hair development" is meant a factor promoting the white hair development, a factor preventing the white hair development or a factor suppressing the white hair development. The results of the research works may possibly be applicable directly to humans, since the research works relate to non-human mammalian animals biologically close to humans. At least, the results will surely propose a potentially indicative finding about the white hair development in humans.

In a seventeenth aspect of the invention, a method for screening for means for controlling the white hair development is provided, the method comprising administering a given candidate substance or a given treatment as means for controlling the white hair development to the model animal causing the white hair development in any of the first aspect through the sixth aspect to examine the effect of such means on suppressing or promoting the white hair development to screen for means for controlling the white hair development in humans and/or non-human mammalian animals.

As in the seventeenth aspect, screening for means for controlling the white hair development in humans or non-human mammalian animals can be done effectively, using the model animal causing the white hair development. The means for controlling the white hair development represents means for promoting the white hair development, means for preventing the white hair development or means for suppressing the white hair development. Such controlling means includes for example the administration of a component for controlling the white hair development in a pharmaceutical formulation such as tablets or internal liquids. By the component for controlling the white hair development is meant a compound exerting an effect on preventing the white hair development, exerting an effect on suppressing the white hair development or exerting an effect on promoting the white hair development. Additionally, the component may be administered for example in the form of a food product containing the component for controlling the white hair development as the controlling means. The means for controlling the white hair development additionally includes various means over a wide range of categories, such as specific treatments, and specific environmental conditions and life style conditions with physiological or psychological influences.

The screening method in the seventeenth aspect may be done singly for screening for means for preventing the white hair development, means for suppressing the white hair development or means for promoting the white hair development. Furthermore, the screening method may be done in combination with a simpler screening method for example a screening method at an in vitro level. Furthermore, the screening method may be done in combination with a more full-scale screening method for example a screening method in human trials with personal consents.

In an eighteenth aspect of the invention, a composition for controlling the white hair development is provided, which contains the following substance (1) or (2) selected by the screening method in the seventeenth aspect as the component for controlling the white hair development.
(1) A substance antagonistic against the substance for preventing the white hair development, the substance for suppressing the white hair development and/or the substance for promoting the white hair development.
(2) A substance for promoting the white hair development.

Any of the means for preventing the white hair development, the means for suppressing the onset thereof, or the means for promoting the onset thereof selected via screening including at least the screening method in the seventeenth aspect may be used as the active component in the composition for controlling the white hair development, as long as the means can be used as a substance to be administered to humans.

BEST MODE FOR CARRYING OUT THE INVENTION

Figure 1:
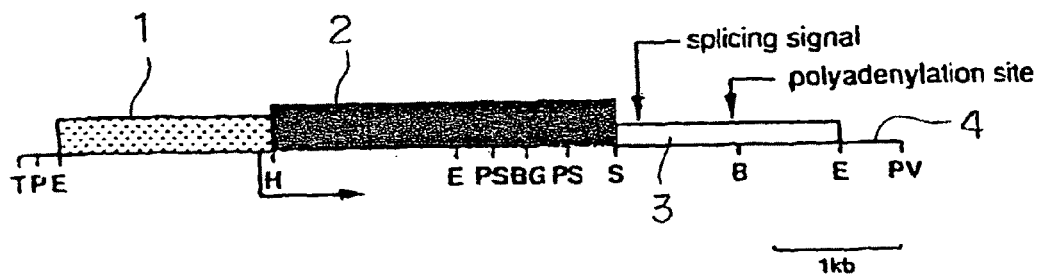
FIG. 1 shows the structure of the plasmid pMT/ret constructed in one Example.

Modes for carrying out the first aspect through the eighteenth aspect including the best modes thereof are described below.

[Model Animal Causing the White Hair Development]

The model animal causing the white hair development in accordance with the invention is a non-human mammalian animal, where the color of the hair first growing after birth is black or almost black, but the model animal has white hair increasingly following aging. Herein, the term "almost black" means a case that "the color is almost black (blackish gray)" and/or a case of "being mostly black with an extremely small part with non-black (for example white) hair". More specifically, the color of the hair first growing after birth is black or almost black but the color of the hair increasingly changes white about one to three months after birth (with some variations in individuals).

Such change of the hair color occurs almost uniformly and gradually over the whole body surface of the mouse in the same pattern as in the white hair development in humans. In other words, only several gray hairs are found among black hairs at the stage of the start of the white hair development. In 8 to 12 months after birth, however, almost all the hairs in the model animal causing the white hair development turn white. The course is very similar to the course of the white hair development in humans.

The model animal causing the white hair development and having such phenotype has a gene type, where (1) the activated RET gene is genetically inserted in a hetero form and (2) the endothelin receptor B (Ednrb) gene is deficient in a hetero form, or the Ednrb gene is deficient in the homo form or in a hetero form and the Ednrb gene is genetically inserted in the homo form or in a hetero form under the DbH promoter.

The animal species of the model animal causing the white hair development as a non-human mammalian animal or the line of the specific animal species thereof is not specifically limited. However, a rodent animal is preferable. Mouse or rat is particularly preferable. Mouse is more particularly preferable.

The type of the activated RET gene is not specifically limited but preferably includes as one example RFP-RET as the hybrid between the RET finger protein (RFP) gene and the activated RET gene. The activated RET gene is conjugated to the downstream of an appropriate promoter such as the metallothionein I promoter, for genetic insertion. The activated RET gene is known from the Literature 1 and the like, as described above. The nucleotide sequence is shown as SQ ID No. 1 in the sequence table.

The Ednrb gene is located on the 14-th chromosome in mouse, and is involved in the onset of megacolon and the differentiation and proliferation of pigment cell. The Ednrb gene is known from the Literature 2 and the like, as described above. The nucleotide sequence is shown as SQ ID No. 2 in the sequence table.

The model animal causing the white hair development in accordance with the invention can be established by preparing an appropriate combination of the method for preparing a transgenic animal, the method for gene targeting or mating, using an appropriate non-human mammalian animal for use in experiments, to obtain the gene type. These procedures themselves never cause any difficulty in skilled persons in the art with expert knowledge and techniques.

Such model animal causing the white hair development is kept and fed under controls at the Chubu University Educational Foundation in Kasugai City, Aichi Prefecture, Japan. Further, the frozen fertilized eggs and frozen sperms from parent animals, by which the model animal causing the white hair development can be prepared via a single mating, are under storage in the National University Corporation Kumamoto University in Kumamoto Prefecture, Japan. The parent animals mean the RET-transgenic animal with the activated RET gene inserted genetically in a hetero form as a non-human mammalian animal and the Ednrb gene-modified animal as the same species of the non-human mammalian animal, where the Ednrb gene is deficient in a hetero form, or the Ednrb gene is deficient in the homo form or in a hetero form and with the Ednrb gene is genetically inserted therein in the homo form or in a hetero form under the DbH promoter.

To a person desiring the use of the model animal causing the white hair development in accordance with the invention or the use of the frozen fertilized eggs/frozen sperms from the parent animals may be supplied the model animal or the frozen fertilized eggs/frozen sperms under reasonable conditions and controls for use.

[Establishing the Model Animal Causing the White Hair Development Via Mating]

In case of intending the establishment of the model animal causing the white hair development via mating, first, the activated RET gene is inserted genetically in a hetero form into a non-human mammalian animal, to prepare an RET-transgenic animal. Then, an Ednrb gene-modified animal as the same species of the non-human mammalian animal is prepared, where the Ednrb gene is deficient in a hetero form, or the Ednrb gene is deficient in the homo form or in a hetero form and the Ednrb gene is genetically inserted in the homo form or in a hetero form under the DbH promoter. Then, the RET-transgenic animal is mated with the Ednrb gene-modified animal, satisfactorily.

The method for preparing the RET-transgenic animal is not limited. As the promoter to which the activated RET gene is conjugated in genetic insertion, there may be used for example the metallothionein I promoter (MT promoter). The MT-RET transgenic mouse with the activated RET gene conjugated to the MT promoter, as genetically inserted therein in a hetero form, can be prepared by the method described below in Example 1. The transgenic mouse with the activated RET gene genetically inserted therein in the homo form generally never reaches delivery.

In case that the model animal causing the white hair development is mouse, the RET-transgenic mouse or the MT/RET transgenic mouse of the line 304, the line 304/B6, the line 192 or the line 242, as described in the Literature 1 or in the following Examples, may preferably be used as the RET-transgenic mouse or the MT/RET-transgenic mouse. RET-transgenic mice or MT/RET-transgenic mice in other lines may also be used as long as these mice are RET-transgenic mice where the activated RET gene is genetically inserted in a hetero form.

The method for preparing the Ednrb gene-modified animal is not limited. By the method described below in Example 2, for example, an Ednrb gene-targeting animal with deficiency in the Ednrb gene in a hetero form can be prepared.

Herein, Ednrb gene-targeting animals with deficiency in the Ednrb gene in the homo form die due to megacolon within several months after birth. However, such megacolon can be prevented by genetically inserting the Ednrb gene under the DbH promoter (dopamine hydroxylase promoter). The Ednrb gene can be genetically inserted in the homo form or in a hetero form under the DbH promoter in an Ednrb gene-targeting animal with deficiency in the Ednrb gene in a hetero form. Such animals never cause the onset of megacolon. Ednrb gene-modified animals thus prepared may also be used as mating parents.

[Establishing the Model Animal Causing the White Hair Development Via Gene Targeting]

The model animal causing the white hair development may also be established by a second establishing method. That is, at first, an RET-transgenic animal or MT/RET-transgenic animal is prepared, where the activated RET gene is inserted genetically in a hetero form. The resulting transgenic animal is treated by a gene targeting procedure for allowing the Ednrb gene therein to be deficient in a hetero form or by a gene modification procedure for allowing the Ednrb gene therein to be deficient in the homo form or in a hetero form and then genetically inserting the Ednrb gene under the DbH promoter. In such manner, the model animal causing the white hair development can be established.

[Establishing the Model Animal Causing the White Hair Development Via Gene Insertion]

The model animal causing the white hair development may also be established by a third establishing method. That is, at first, an Ednrb gene-modified animal is prepared, where the Ednrb gene therein is deficient in a hetero form, or the Ednrb gene therein is deficient in the homo form or in a hetero form and the Ednrb gene is genetically inserted in the homo form or in a hetero form under the DbH promoter. Then, a gene insertion procedure is done for genetically inserting the activated RET gene (or the activated MT/RET gene) in the resulting Ednrb gene-modified animal. In such manner, the model animal causing the white hair development can be established.

For gene insertion of the activated RET gene (or the activated MT/RET gene) in general non-human mammalian animals, additionally, the number of inserted transgenes (copy number) is 2 or more in many cases. For gene insertion of the activated RET gene (or the activated MT/RET gene) in the Ednrb gene-modified animal using a knock-in procedure, however, the copy number is 1. In that case, the resulting animal may potentially not be any model animal spontaneously causing the white hair development, because the copy number of the activated RET gene is small.

[Successive Growing of the Model Animal Causing the White Hair Development]

Via mating together the model animal causing the white hair development established by the various methods described above, the model animal causing the white hair development can be stably grown successively. In this case, the probability of obtaining the model animal causing the white hair development via mating is ⅓.

[Method for Making Research Works about the White Hair Development]

Various research works can be done about the white hair development in various non-human mammalian animals or humans, using the model animal causing the white hair development. First, the scarcely elucidated mechanism of white hair development can be investigated per se. Second, it can specifically be certified in the relation with the elucidation of the mechanism of white hair development, whether or not the administration of a given substance to the model animal causing the white hair development functions to suppress the white hair development or to promote the white hair development or whether or not the administration thereof has no relation with the white hair development. Third, it can specifically be certified whether or not a given treatment of the model animal causing the white hair development functions to suppress the white hair development or to promote the white hair development or whether or not a given treatment has no relation with the white hair development.

[Method for Screening for Means for Controlling the White Hair Development]

In a mode of making a more practical research work in the research works about the white hair development, screening for various means for controlling the white hair development and functioning to suppress or promote the white hair development can be done.

Specifically, the administration of a given candidate substance or a given treatment as means for preventing the white hair development, means for suppressing the white hair development or means for promoting the white hair development is done to examine the effect of those means on the suppression or the promotion of the white hair development. In such manner, screening for means for controlling the white hair development in humans and/or non-human mammalian animals can be done. By the means for controlling the white hair development is meant means for suppressing the onset thereof, means for preventing the onset thereof or means for promoting the onset thereof. Such screening has first been achieved by the provision of the model mouse causing the white hair development.

[Composition for Controlling the White Hair Development]

When it is certified by the screening method that a substance functions to suppress the white hair development, compositions for controlling the white hair development (for preventing white hair development) such as pharmaceutical agents, food products and cosmetic products containing the substance as the active component can be provided.

In case that a substance functioning to promote the white hair development is verified, additionally, a substance (antagonist) functioning in a manner antagonistic against the substance (agonist) is investigated, to provide compositions for controlling the white hair development (for preventing white hair development) such as pharmaceutical agents, food products and cosmetic products containing the substance as the active component.

Further, the substance per se functioning to promote the white hair development is an important research tool for the onset thereof. For individuals disliking an intermediate gray-haired state (so-called "gray-white-flecked hair"), the substance may be useful sometimes as a component for promoting the transfer to a complete white-haired state. Therefore, compositions for controlling the white hair development (for promoting white hair development) such as pharmaceutical agents, food products and cosmetic products containing the substance as the active component can be provided.

EXAMPLES

The Examples of the invention are now described. The technical scope of the invention is never limited by the following Examples.

Example 1

Preparation of MT/RET Transgenic Mouse

The preparation of the MT-RET-transgenic mouse described below in Example 1 was essentially done, according to the method in the Literature 1. Herein, the mouse of the line 304/B6 as described below is described in the following Literature 6.
[Literature 6] Kato M, Takahashi M, Akhand A A, Lie W, Dai Y, Shimizu S, Iwamoto T, Suzuki H, Nakashima I, "Transgenic mouse model forskin malignant melanoma" Oncogene, 1998 Oct. 8; (14); 1885-8.
(Plasmid Construction)

A 1.7-kb EcoRI-Bg/II fragment containing the murine metallothionein I (MT-I) promoter was scissored out from the plasmid pMK (Brinster et al., 1981) and subcloned into the polylinker site of the plasmidpUC8. Then, a 340-bp PvuII-Hind III fragment corresponding to the SV-40-controlling region in the plasmidpSV2RETT (Takahashi et al., 1988) was replaced with the MT-I promoter-containing PvuII-Hind III fragment subcloned in pUC8, to construct a plasmid pMT/RET. The plasmid pMT/RET contains a transgene MT/RET as the activated RET gene conjugated to the MT-I promoter region.

FIG. 1 shows the structure of pMT/RET. In FIG. 1, box 1 shows the murine metallothionein I promoter (MT-I promoter); box 2 shows the cDNA of the activated RET gene; box 3 shows the SV-40 sequence; and line 4 shows the sequence of the vector. Symbols for the restriction enzymes (endonucleases) shown in the figures are as follows: B: Bam HI; BG: Bg/II; E: EcoRI; H: Hind III; P: Pvu II; PS: Pst I; PV: PvuI; S: Sma I; T: Tth111I. The arrow toward right side shows the origin of transcription as positioned on an upstream by 84 bp from the Hind III site.
(Establishment of Transgenic Mouse Line)

A 6.9-kb Tth111I-PvuI fragment (pMT/RET) was micro-injected in a fertilized egg between BCF1 mice [(BALB/cx C57BL/6)×BALB/c] as provided by the Experimental Animal Institution, the Department of Medicine, the National University Corporation Nagoya University. These fertilized eggs were transplanted into a female DDY in false pregnancy, to obtain 17 founder mouse individuals with the MT/RET transgene inserted therein. The method for the micro-injection, embryonic transplantation and DNA analysis were done according to the method by Hogan et al. (Hogan et al., 1986).

The following four lines among these founder mice were established as MT/RET-transgenic mice, where the activated RET gene was genetically inserted in a hetero form. Several years after the preparation of the mouse of the line 304, mating between the line 304 mouse and the C57BL/6 line mouse was repeatedly done, to prepare the 304/B6 line. The MT/RET transgenic mice of these four lines never cause any color change of the body hair throughout their lives. However, white hair may emerge at about 1% at their aging stage.
1) The line 192: females with a transgene copy number of 14, where melanosis and melanocyte tumors unavoidably emerge.
2) The line 242: males with a transgene copy number of 4, where melanosis emerges but no tumors develop.
3) The line 304: males with a transgene copy number of 5, where melanosis and melanocyte tumors unavoidably emerge.
4) The line 304/B6: as obtained from mating between the C57BL/6 mouse and the MT/RET-transgenic mouse of the line 304. About 3 to 4 months after birth, benign melanocyte tumors unavoidably emerge.

Example 2

Preparation of Ednrb Gene-Targeting Mouse

The preparation of the Ednrb gene-targeting mouse in accordance with the Example is done according to the method of the Literature 2 as described above. The summary is described hereinbelow.
[Construction of Gene Targeting Vector]

Figure 2:
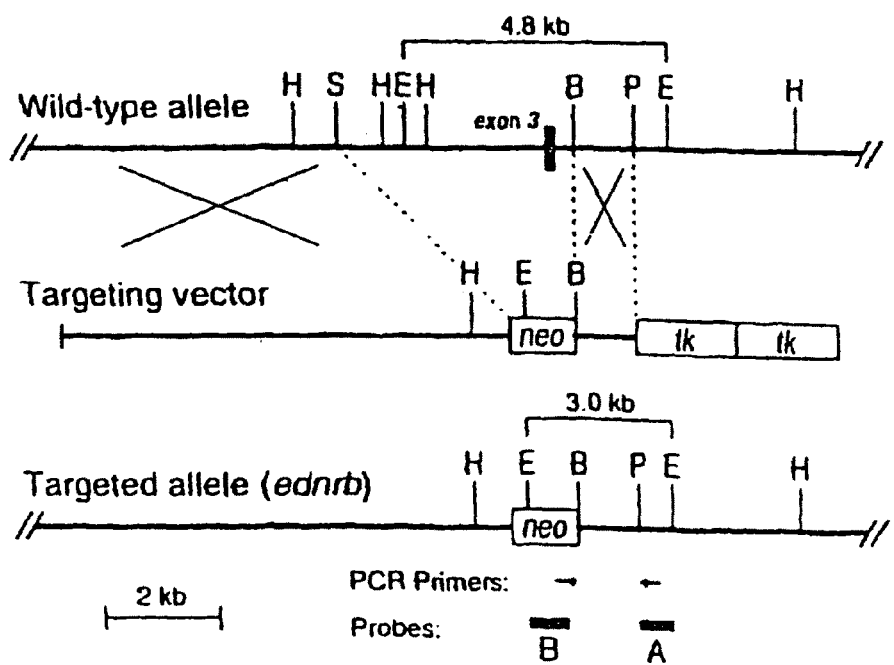
FIG. 2 shows the structure of the targeting vector and the like as constructed in one Example.

As the "wild-type allelle" in FIG. 2, a map including the Ednrb exon 3 in the murine genome DNA is shown. The Roman symbols in the map, such as H, S and B represent recognition sites of specific restriction enzymes, as follows. B: BglII; E: EcoRI; H: HindIII; S: SalI; P: PstI.

As "the targeting vector" in FIG. 2, a vector for recombination as constructed for targeting the Ednrb gene of the murine ES cell is shown. The vector for recombination is prepared by replacing a 4.2-kb region containing the Ednrb exon 3 of the murine genome DNA cloned with a neomycin-resistant cassette [represented as "neo"] and then conjugating the tk cassette (simple herpes virus thymidine kinase) at the 3' end of the resulting construct for screening for positivity/negativity (Ishibashi et al., 1993).

The genome DNA region in case of the occurrence of the intended Ednrb gene targeting is shown as "Targeted allele (ednrb)" in FIG. 2. In the bottom of FIG. 2, a probe for southern blotting and the location of the PCR primer are shown together.
(Preparation of Gene Targeting Mouse)

A JH-1 murine ES cell line (Rosahl et al., 1993) was cultured on a feeder layer. The Ednrb gene was subjected to electroporation, together with the targeting vector. According to the description of "Ishibashi et al., 1993", then, a double resistance assay against G418 and FIAU using the tk cassette was employed for screening for the ES cell.

Screening for the ES cell clone with double resistance was done with the designated 5' neo-primer and 3' primer. The micro-injection of a blastocyst and the preparation of a chimera mouse were done according to the description of "Rosahl et al., 1993". In the present Example, detailed parts never described therein were done according to the Literature 2.

Melanocyte proliferation and melanin generation were inhibited in a gene targeting mouse with deficiency in the Ednrb gene in the homo form among the resulting Ednrb gene targeting mice, so that megacolon emerged in the mouse before growing, leading to its death. In the Ednrb gene-targeting mouse with deficiency in the Ednrb gene in a hetero form, melanocyte proliferation and melanin generation occurred with no apparent difference from those in the wild type, so that the mouse grew with no occurrence of megacolon. Thus, the mouse was used for the following mating as a parent for the model mouse causing the white hair development.

Furthermore, the hairs first growing in the gene targeting mouse with deficiency in the Ednrb gene in the homo form were mostly white, where black spots were partially mixed. All the hairs first growing in the gene targeting mouse with deficiency in the Ednrb gene in a hetero form were black hairs.

Example 3

Mating

The MT/RET-transgenic mouse of the line 304/B6 as obtained in Example 1 (with the activated RET gene genetically inserted therein in a hetero form) was mated with the Ednrb gene-targeting mouse obtained in Example 2 (with deficiency in the Ednrb gene in a hetero form).

Via the mating, it is theoretically suggested that F1 generations with the following four gene types described below in (1) through (4) may be obtained.
(1) RET/+·Ednrb(+/−): the gene type where the activated RET gene is inserted genetically in a hetero form while the Ednrb gene is deficient in a hetero form.
(2) RET/+·Ednrb(+/+): the gene type where the activated RET gene is inserted genetically in a hetero form while the Ednrb gene is not deficient.
(3) +/+·Ednrb(+/−): the gene type where the activated RET gene is never inserted while the Ednrb gene is deficient in a hetero form.
(4) +/+·Ednrb(+/+): the gene type where the activated RET gene is never inserted while the Ednrb gene is never deficient.

Consequently, a model mouse with the gene type described above in (1) as verified by the analysis of the gene type could be established as the grown F1 generation. The color of the hair of the model mouse first growing after birth was black. However, the change of the hair color to white began about one to 3 months after birth. About 12 to 18 months after birth, almost all the hairs turned white, although some difference was observed in the individuals.

Figure 3:
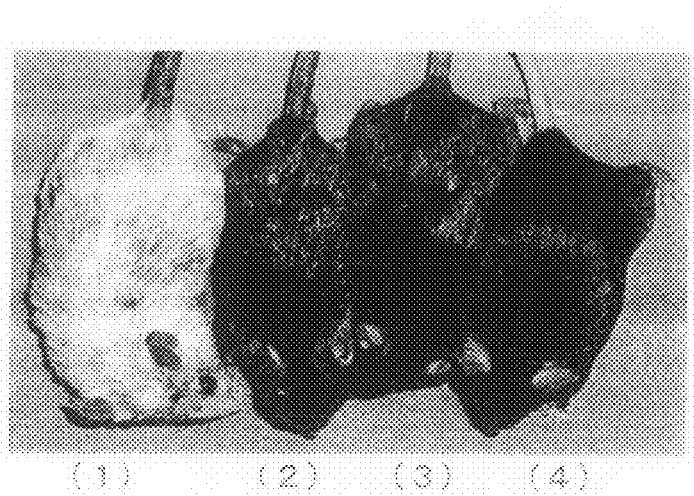
FIG. 3 shows the photograph of the model mouse causing the white hair development in the Example.

The photograph of the model mouse causing the white hair development and having the gene type described above in (1), after the hair turned white, is shown in FIG. 3 (1). FIG. 3 (2) shows the mouse with the gene type described above in (2). FIG. 3 (3) shows the mouse with the gene type described above in (3). FIG. 3 (4) shows the mouse with the gene type described above in (4). The hair of the model mouse causing the white hair development as shown in FIG. 3 (1) when the hair first grew after birth was black or almost black like the mice shown in FIG. 3 (2) through (4).

Figure 4:
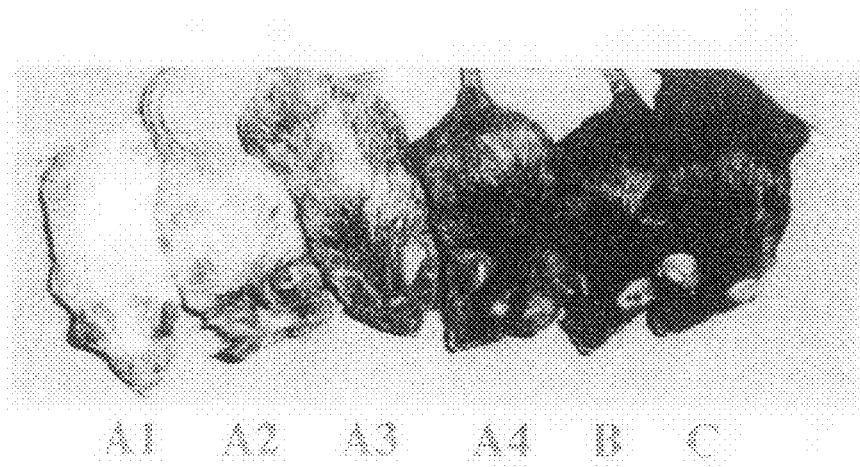
FIG. 4 shows the photographs depicting the course of the white hair development in the model mouse causing the white hair development in the Example.

The change of the hair color in the model mouse causing the white hair development and having the gene type described above in (1) over time is described with reference to FIG. 4. Six mice shown in FIG. 4 are the mice individually described below in 1) through 3).
1) The mouse on the right end as shown as "C" in FIG. 4 is depicted for comparison, and the mouse is 15 months after birth and has the gene type "+/+·Ednrb (+/−)" described above in (3).
2) The mouse on the second from the right end as shown as "B" in FIG. 4 is depicted also for comparison, and the mouse is 8 months after birth and has the gene type "RET/+·Ednrb (+/+)" described above in (2).
3) The mice on the third through sixth from the right end in FIG. 4 are mice with the gene type described above in (1) with different ages in month. Specifically, the mouse on the third from the right end as shown as "A4" in FIG. 4 is 3 months after birth; the mouse on the fourth from the right end as shown as "A3" in FIG. 4 is six months after birth; the mouse on the fifth from the right end as shown as "A2" in FIG. 4 is 8 months after birth; and the mouse on the sixth from the right end as shown as "A1" in FIG. 4 is 10 months after birth.

FIG. 3 and FIG. 4 clearly show that the model mouse causing the white hair development in accordance with the invention has a phenotype such that "the color of the hair first growing after birth is black or almost black but the model animal causes the spontaneous white hair development following aging".

Since FIG. 3 and FIG. 4 are monochrome photographs, the flash light for photography is reflected on a certain part of the black hair in the mice, so that the part is imaged rather whitish. However, these parts imaged whitish are actually black.

In accordance with the invention, there can be provided a model mouse causing the white hair development most suitable for research works about the mechanism of the white hair development in humans, a pharmaceutical preparation capable of effectively preventing the white hair development or a treatment thereof.

What is claimed is:

1. A model mouse which has a phenotype such that the color of the hair first growing after birth is black or gray and the model mouse then undergoes extensive white hair development following aging as compared to a wild type or control mouse of the same age which does not significantly develop white hair after aging, whereby the model mouse has a genotype in which an activated RET gene is genetically inserted in a heterozygous form and the endothelin receptor B gene is deficient in a heterozygous form.

2. A model mouse causing the white hair development according to claim 1, where the activated RET gene is RFP-RET as the hybrid between the RFP gene and the activated RET gene.

3. A model mouse causing the white hair development according to claim 1, where the activated RET gene is conjugated with the metallothionein I gene as the promoter.

* * * * *